United States Patent
Glazer

(10) Patent No.: US 9,367,704 B2
(45) Date of Patent: Jun. 14, 2016

(54) APPARATUS AND METHODS FOR DISPLAYING INFORMATION REGARDING OBJECTS

(71) Applicant: Yariv Glazer, Be'er Tuvia (IL)

(72) Inventor: Yariv Glazer, Be'er Tuvia (IL)

( * ) Notice: Subject to any disclaimer, the term of this patent is extended or adjusted under 35 U.S.C. 154(b) by 0 days.

(21) Appl. No.: 14/202,030

(22) Filed: Mar. 10, 2014

(65) Prior Publication Data

US 2015/0254470 A1    Sep. 10, 2015

(51) Int. Cl.
  *G06F 21/62*  (2013.01)
  *G06Q 50/24*  (2012.01)
  *G06F 19/00*  (2011.01)

(52) U.S. Cl.
  CPC .......... *G06F 21/6218* (2013.01); *G06F 19/322* (2013.01); *G06Q 50/24* (2013.01); *G06F 2221/2111* (2013.01)

(58) Field of Classification Search
  CPC .... G06F 21/6218; G06F 19/322; G06Q 50/24
  USPC ...................................................... 726/20–27
  See application file for complete search history.

(56) References Cited

U.S. PATENT DOCUMENTS

| | | | |
|---|---|---|---|
| 2002/0164997 A1* | 11/2002 | Parry ............................ | 455/456 |
| 2003/0217122 A1* | 11/2003 | Roese et al. .................. | 709/219 |
| 2007/0268138 A1* | 11/2007 | Chung et al. ............... | 340/572.1 |
| 2009/0178144 A1* | 7/2009 | Redlich et al. ................. | 726/27 |
| 2009/0206992 A1* | 8/2009 | Giobbi et al. ................ | 340/5.74 |
| 2011/0164569 A1* | 7/2011 | Bamberger et al. .......... | 370/328 |

* cited by examiner

*Primary Examiner* — Amir Mehrmanesh
(74) *Attorney, Agent, or Firm* — Thomas Heed

(57) ABSTRACT

Apparatus, and methods utilizing such apparatus, are described for displaying information regarding an object including a terminal for collecting, manipulating, and displaying information regarding the object, and a location processor for determining the location of the terminal with respect to the object. The apparatus further includes an access processor programmed to deny a user of the terminal access to the information when the distance between the terminal and the object exceeds a specified value. The apparatus and methods are particularly useful when implemented in a hospital setting in which the user is a medical provider, the object is a patient, and the terminal is a mobile terminal.

14 Claims, 4 Drawing Sheets

APPARATUS AND METHODS FOR DISPLAYING INFORMATION REGARDING OBJECTS

RELATED APPLICATION

This application is a continuation application of U.S. Provisional Application No. 61/778,422, filed Mar. 13, 2013, and incorporates by reference the disclosure therein.

FIELD AND BACKGROUND OF THE INVENTION

The present invention relates to apparatus, and to methods utilizing such apparatus, for displaying information regarding objects, and particularly to such apparatus and methods useful in a hospital setting.

Physicians and medical providers examine patients several times per day in various patient settings, such as hospital wards. During each round, the physicians move along a public corridor, entering each room to examine the status of the patient(s) and equipment in the room. Each such system thus includes a plurality of wards, each including a plurality of patient rooms, arranged along a public pathway (corridor), and a database in which information regarding object(s), such as patients and equipment, is stored.

Various types of systems have been developed to prevent contamination and/or breach of privacy.

In one type of system, an enclosure, pliable or rigid, is applied over a terminal to prevent physical contamination, and is disposed after exposed to the patient. As one example, an enclosure, such as a bag or sleeve, is applied over a thermometer when used for measuring the temperature of a patient, and is disposed after the enclosure has been exposed to the patient. In this example, a visual or audible alarm is activated when the thermometer is not protected by the enclosure.

Another type of system is used to prevent a breach of privacy. For example, in a system including a plurality of wards arranged along a public corridor, a terminal, used for reviewing and updating information stored in the database with respect to the object(s) in the wards, is automatically locked when not used for a specified time. The terminal may also be locked when an authorized logged-in user is located at a distance greater than one specified, thereby requiring the user to re-login. If the required re-logins become too frequent, the user may become disinclined to use this type of system in view of the interference with workflow.

OBJECTS AND BRIEF SUMMARY OF THE PRESENT INVENTION

An object of the present invention is to provide apparatus and methods for displaying information regarding objects having advantages in one or more of the above respects.

According to one broad aspect of the present invention, there is provided apparatus for displaying information regarding the object, comprising: a terminal for collecting, manipulating, and displaying information regarding the object; and a location processor for determining the location of the terminal with respect to the object; characterized in that the apparatus further comprises an access processor, programmed to deny a user of the terminal access to the information, when the distance between the terminal and the object exceeds a specified value.

In some systems described below, the apparatus further comprises an enclosure designed to be received over the terminal to protect the terminal and the object against physical contamination. In other systems described below, the apparatus further comprises an enclosure designed to be received over the user to protect the user and the object against physical contamination. With respect to both systems, the access processor is also programmed to lock the terminal against further use, when the distance between the terminal and the object exceeds the specified value, until the enclosure is removed.

According to a more specific aspect of the invention, there is provided apparatus for displaying information regarding an object, comprising: a terminal for collecting, manipulating, and displaying information regarding the object; and a location processor for determining the location of the terminal with respect to the object; characterized in that the apparatus further comprises an access processor programmed to deny a user of the terminal access to the information, when the distance between the terminal and the object exceeds a specified value, and still further comprises an enclosure designed to be received over the terminal to protect the object and the terminal against physical contamination.

In the preferred embodiments described below, the apparatus is designed for use in a hospital setting in which the user is a medical provider, the object is a patient, and the terminal is a mobile terminal. Such a hospital setting is preferably used when there are a plurality of patients in a plurality of medical wards, and when there are a plurality of mobile terminals.

According to another broad aspect of the present invention, there is provided a method for displaying information regarding an object, comprising: utilizing a terminal for collecting, manipulating, and displaying information regarding the object; and utilizing a location processor for determining the location of the terminal with respect to the object; characterized in that an access processor is programmed to deny a user of the terminal access to the information when the distance between the terminal and the object exceeds a specified value.

Particularly good results are obtainable in systems wherein the terminal includes a display panel for displaying the information regarding the object; and wherein the terminal is a mobile terminal. In such systems, while the mobile terminal moves along the longitudinal axis of a corridor, the location processor detects the location of the mobile terminal along the corridor. In addition, status information of the patients in the rooms that are upcoming is compiled and displayed in top blocks of the display panel; the status information of the patients in the rooms that are aligned with the mobile terminal is compiled and displayed in middle blocks of the display panel; and the status information of the patients in the rooms that have been passed is compiled and displayed in bottom blocks of the display panel.

Several preferred embodiments of the invention are described below for purposes of example.

BRIEF DESCRIPTION OF THE DRAWINGS

The invention is herein described, by way of example only, with reference to the accompanying drawings, wherein.

DESCRIPTION OF PREFERRED EMBODIMENTS

Figure 1:
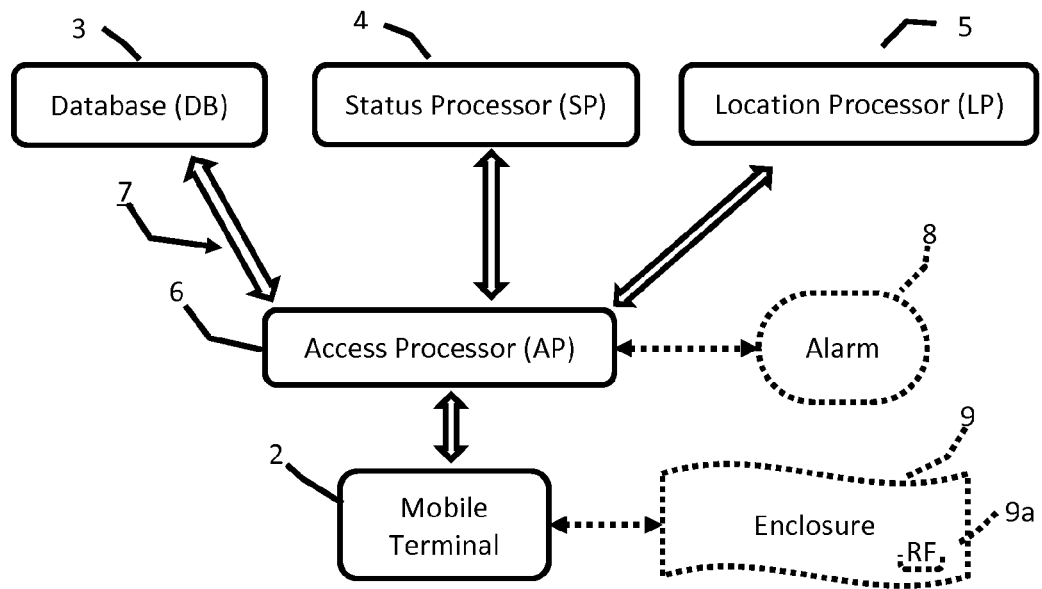
FIG. 1 is a block diagram schematically illustrating one type of system constructed and operative in accordance with the present invention.
Figure 2:
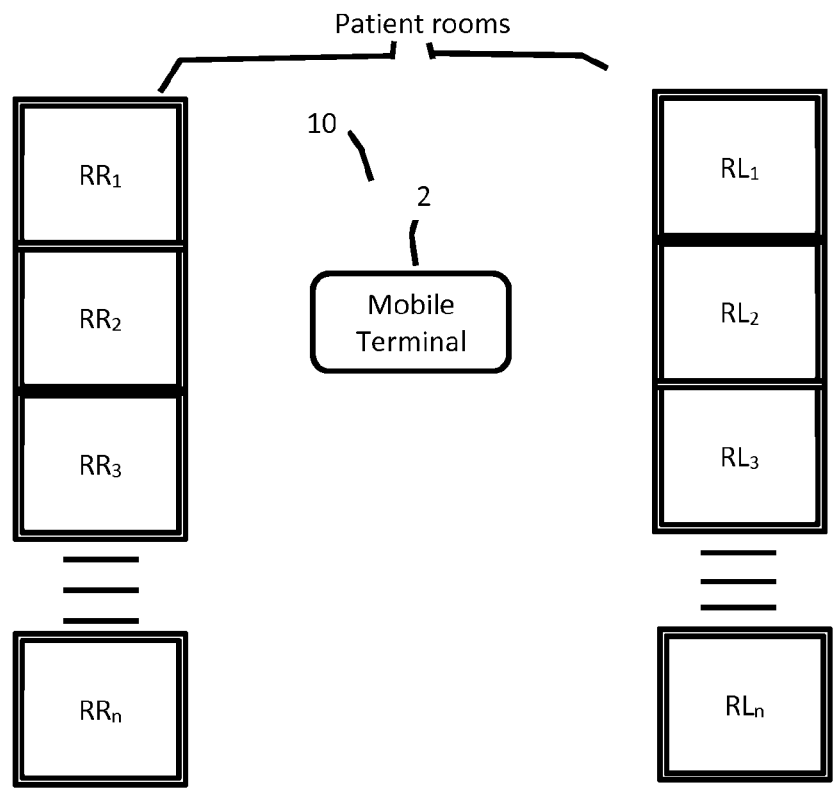
FIG. 2 is a block diagram more particularly illustrating the construction of a ward subsystem useful in the system of FIG. 1.

As indicated earlier, FIG. 1 is a block diagram schematically illustrating the basic structure and operation of a system constructed and operative in accordance with the present invention, and FIG. 2 is a corresponding diagram of a ward subsystem used therein.

Thus, as shown in FIG. 1, the illustrated system includes a terminal 2 (a mobile terminal in this case) for collecting, manipulating, and displaying information regarding an object, such as a person (e.g., a patient) or an article of equipment; a database 3 for storing the information; a status processor 4 for processing and compiling information regarding the object; and a location processor 5 for determining the location of the terminal 2 with respect to the object.

As shown in FIG. 2, the illustrated known ward-subsystem includes a plurality of patient rooms 10a, arranged on opposite sides of a corridor 10b; thus, FIG. 2 illustrates one line of rooms RR1-RRn on one side of the corridor 10b, and another line of rooms RL1-RLn on opposite side of the corridor.

According to the present invention, the illustrated system further includes an access processor 6 (FIG. 1) programmed to deny a user of the terminal (namely any medical caregiver, such as a physician or a nurse) access to such information when the distance between the terminal and the object exceeds a specified value. As described below, such a system provides advantages in protecting the privacy of persons (e.g., patients) by preventing specific information regarding the person to be viewed by unauthorized parties.

FIG. 1 also illustrates two optional additions to such a system: an alarm, as indicated by the broken lines 8; and an enclosure carrying an RF identification chip, as indicated by broken lines 9 and 9a, respectively. As described below, using these options enables the system to alert a user regarding the need to replace a contaminated enclosure when a user leaves the room.

As shown in FIG. 2, the mobile terminal 2 is carried by the user along the longitudinal axis of a corridor 10b between the two lines of rooms. As the mobile terminal 2 is moved by the user along corridor 10b, its location with respect to the two lines of rooms 10a is continuously determined by the location processor 5.

Figure 3:
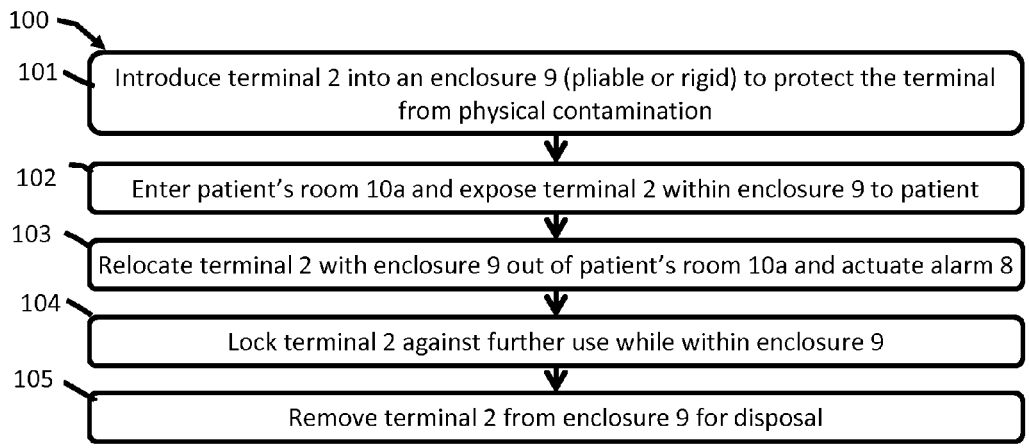
FIG. 3 is a flowchart illustrating one example of the operation of the system of FIG. 1.

FIG. 3 is a flowchart illustrating one example of the operation of the system of FIGS. 1 and 2. In this example, terminal 2 is introduced into an enclosure 9 (pliable or rigid) to protect the terminal from physical contamination. The user, while carrying terminal 2, enters a patient room 10a and exposes the terminal 2 with enclosure 9 to a patient. If the user relocates terminal 2 with enclosure 9 out of the patient's room 10a, alarm 8 is actuated; and the terminal 2 is locked against further use while within enclosure 9. The terminal 2 remains locked until it is removed from enclosure 9.

Figure 4:
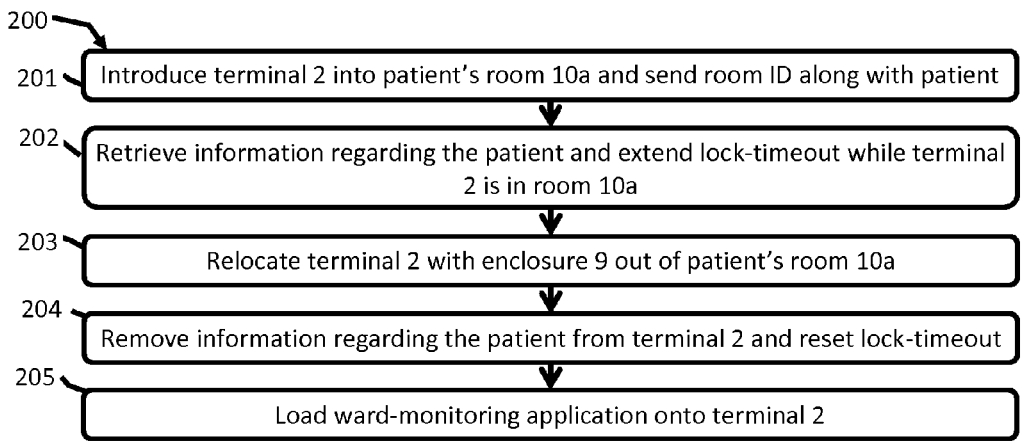
FIG. 4 is a flowchart illustrating another example of the operation of the system of FIG. 1.

FIG. 4 is a flowchart illustrating an example of the operation of a ward-subsystem in the diagram of FIG. 2. Thus, as shown in FIG. 4, whenever the user introduces terminal 2 into a patient's room 10a, the location processor 5 determines the location of the terminal 2 and thus identifies the respective patient's room ID in which the terminal is located. The ID of the patient(s) within each room is stored in the database 3.

When the terminal 2 is carried into a patient's room, the terminal requests access to patient information. The access processor 6 retrieves the location of the terminal and the associated room ID. The access processor then queries the database 3 for the patient ID to allow access to information regarding the patient. The access processor also extends the lock-timeout while the terminal is in the room.

As soon as the terminal 2 is relocated out of the patient's room 10a, the patient information regarding the patient in the room is removed from the terminal. The lock-timeout is then reset, and the ward-monitoring application of FIG. 2 is loaded onto the terminal.

Figure 5:
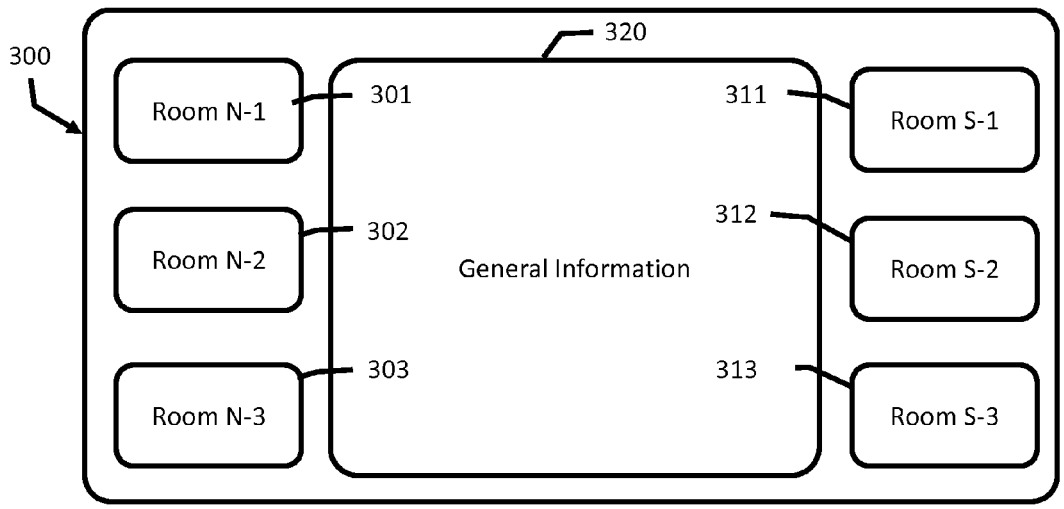
FIG. 5 is a block diagram illustrating the display on the display panel of a terminal in FIG. 2.

FIG. 5 is a block diagram illustrating the display on the display panel of the terminal in FIG. 2. As shown in FIG. 5, the display panel 300 displays a line of room 301-303 on one side of the display panel and another line of rooms 311-313 on the other side of the display panel. The two lines are separated by a central region 320 for displaying general information.

Figure 6:
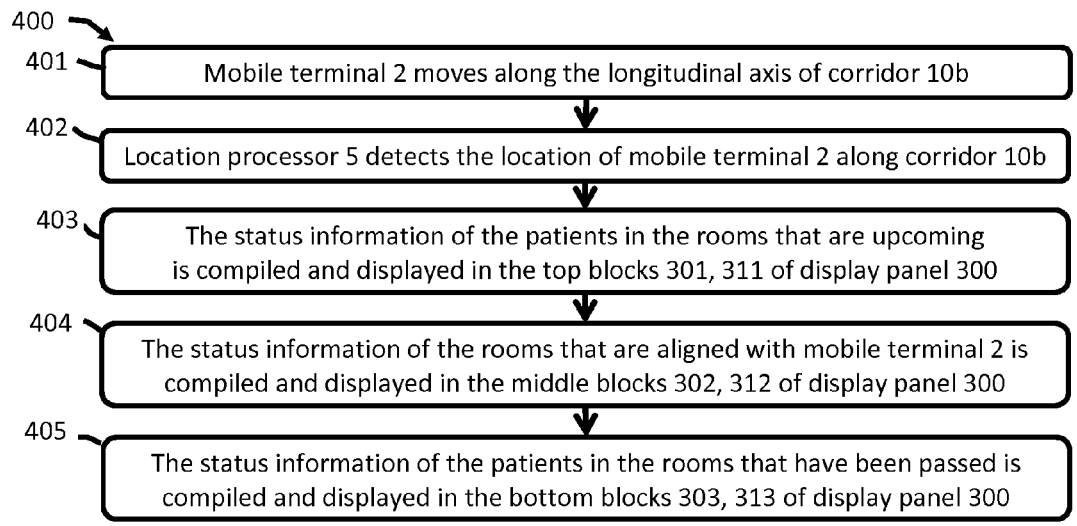
FIG. 6 is a flowchart illustrating an example of the operation of the ward-subsystem of FIG. 2.

FIG. 6 is a flowchart illustrating an example of the operation of the ward-subsystem of FIG. 2. Thus, as shown in FIG. 6, as the mobile terminal 2 is carried along the longitudinal axis of corridor 10b, the location processor 5 detects the location of the mobile terminal in the corridor. The status information of the patients in the rooms that are upcoming is compiled and displayed in the top blocks 301, 311 of the display panel 300; the status information of the rooms that are aligned with the mobile terminal 2 is compiled and displayed in the middle blocks 302, 312 of the display panel 300; and the status information of the patients in the rooms that have been passed is compiled and displayed in the bottom blocks 303, 313 of the display panel 300.

Figure 7:
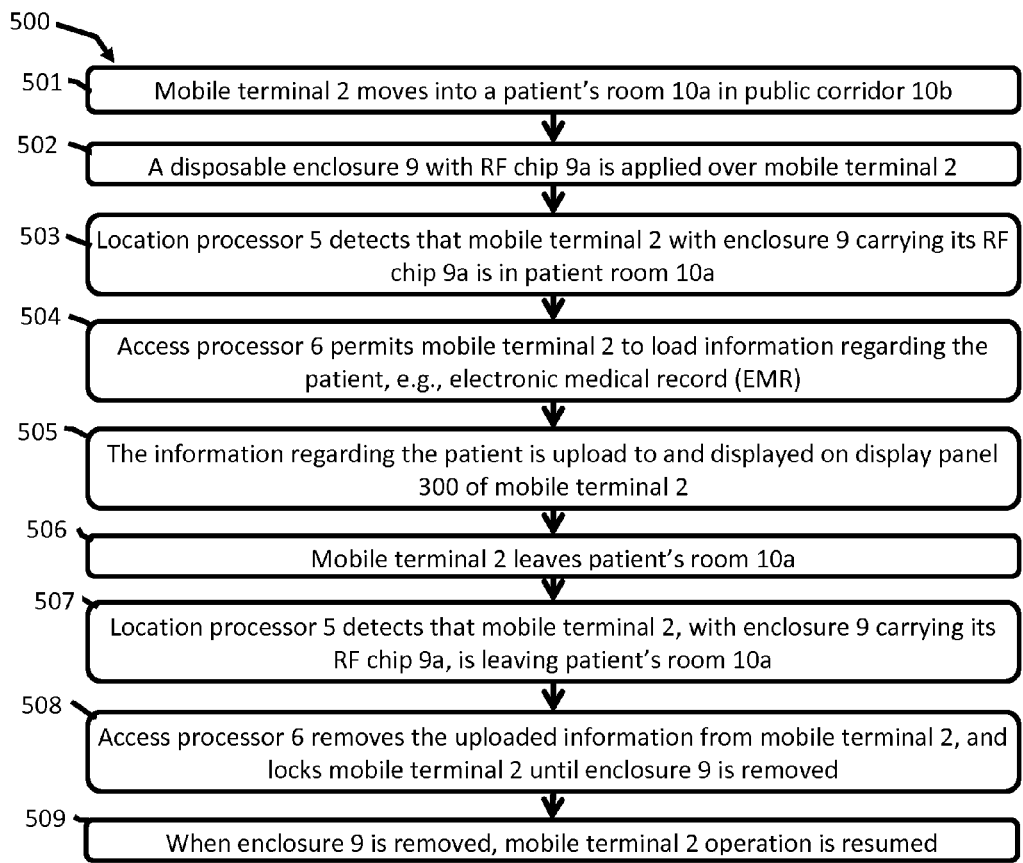
FIG. 7 is a flowchart illustrating another example of the operation of the ward-subsystem of FIG. 2

FIG. 7 is a flowchart illustrating another example of the operation of the ward-subsystem of FIG. 2. Thus, as shown in FIG. 7, as the mobile terminal 2 is carried into a patient's room 10a in public corridor 10b, a disposable enclosure 9 with an RF chip 9a is applied over the mobile terminal. The location processor 5 detects that the mobile terminal, with its enclosure 9 carrying its RF chip 9a, is in the patient's room 10a. The access processor 6 then permits mobile terminal 2 to load information, e.g., electronic medical records (EMR), regarding the patient residing in the room. The information regarding the patient is upload into, and displayed on, the display panel 300 of the mobile terminal.

As soon as the location processor 5 detects that the mobile terminal 2, with the enclosure 9 carrying its RF chip 9a, is leaving the patient's room 10a, the access processor 6 removes the uploaded information from the mobile terminal and locks the mobile terminal until the enclosure 9 is removed. When the enclosure 9 is removed, the mobile terminal 2 operation is resumed.

While the invention is herein described with respect to several preferred embodiments, it will be appreciated that these are set forth merely for purposes of example, and that many other variations, modifications and applications of the invention may be made.

What claimed is:

1. An apparatus for displaying information regarding an object, comprising:
    a terminal for collecting, manipulating, and displaying information regarding the object; and a location processor for determining the location of the terminal with respect to the object;
    characterized in that said apparatus further comprises an access processor, programmed to deny a user of the terminal access to said information, when the distance between the terminal and the object exceeds a specified value;

wherein said terminal comprises a display panel for displaying said information regarding the object; wherein said terminal is a mobile terminal; and wherein, while the mobile terminal moves along the longitudinal axis of a corridor:
the location processor detects the location of the mobile terminal along the corridor; the status information of the patients in the rooms that are upcoming is compiled and displayed in top blocks of the display panel;
the status information of the rooms that are aligned with the mobile terminal is compiled and displayed in middle blocks of the display panel;
and the status information of the patients in the rooms that have been passed is compiled and displayed in bottom blocks of the display panel.

2. The apparatus according to claim 1, further comprising an enclosure designed to be received over the terminal to protect the object and the terminal against physical contamination.

3. The apparatus according to claim 1, wherein said apparatus further comprises an enclosure designed to be received over the terminal to protect the terminal and the object against physical contamination.

4. The apparatus according to claim 1, wherein said apparatus further comprises an enclosure designed to be received over the user to protect the user and the object against physical contamination.

5. The apparatus according to claim 1, wherein said access processor is programmed also to lock the terminal against further use, when said distance between the terminal and the object exceeds said specified value, until said enclosure is removed.

6. The apparatus according to claim 1, wherein said access processor is programmed also to lock the terminal against further use, when said distance between the terminal and the object exceeds said specified value, until said enclosure is removed.

7. The apparatus according to claim 1, wherein said apparatus further comprises a second enclosure designed to be received over the user to protect the user and the object against physical contamination.

8. A Method for displaying information regarding an object, comprising:
utilizing a terminal for collecting, manipulating, and displaying information regarding the object; and utilizing a location processor for determining the location of the terminal with respect to the object;
characterized in programming an access processor to deny a user of the terminal access to said information when the distance between the terminal and the object exceeds a specified value;
wherein said terminal includes a display panel for displaying said information regarding the object; wherein said terminal is a mobile terminal; and wherein, while the mobile terminal moves along the longitudinal axis of a corridor:
the location processor detects the location of the mobile terminal along the corridor;
the status information of the patients in the rooms that are upcoming is compiled and displayed in top blocks of the display panel;
the status information of the rooms that are aligned with the mobile terminal is compiled and displayed in middle blocks of the display panel;
and the status information of the patients in the rooms that have been passed is compiled and displayed in bottom blocks of the display panel.

9. The method according to claim 8, wherein said method is implemented in a hospital setting in which the user is a medical provider, the object is a patient, and the terminal is a mobile terminal.

10. The method according to claim 9, wherein there are a plurality of patients in a plurality of medical wards, and wherein there are a plurality of mobile terminals.

11. The method according to claim 8, wherein said method further utilizes an enclosure designed to be received over the terminal to protect the terminal and the object against physical contamination.

12. The method according to claim 8, wherein said method further utilizes an enclosure designed to be received over the user to protect the user and the object against physical contamination.

13. The method according to claim 11, wherein said access processor is programmed also to lock the terminal against further use, when said distance between the terminal and the object exceeds said specified value, until said enclosure is removed.

14. The method according to claim 12, wherein said access processor is programmed also to lock the terminal against further use, when said distance between the terminal and the object exceeds said specified value, until said enclosure is removed.

* * * * *